United States Patent [19]
Goto et al.

[11] Patent Number: 5,169,856
[45] Date of Patent: Dec. 8, 1992

[54] PIPERIDINOALKYL DERIVATIVES OF CARBOXYLIC ACID AMIDES

[75] Inventors: Giichi Goto, Osaka; Akinobu Nagaoka, Hyogo, both of Japan

[73] Assignee: Takeda Chemical Industries, Inc., Osaka, Japan

[21] Appl. No.: 306,579

[22] Filed: Feb. 6, 1989

[30] Foreign Application Priority Data

Feb. 15, 1988 [JP] Japan ................................ 63-32339
May 11, 1988 [JP] Japan ................................ 63-114169

[51] Int. Cl.$^5$ ................. A61K 31/445; C07D 401/12; C07D 409/12; C07D 407/12
[52] U.S. Cl. ....................... 514/331; 514/248; 514/252; 514/256; 514/258; 514/259; 514/260; 514/269; 514/272; 514/274; 514/275; 514/318; 514/319; 514/320; 514/321; 514/322; 514/323; 514/324; 514/326; 544/235; 544/237; 544/238; 544/253; 544/297; 544/298; 544/299; 544/301; 544/302; 544/303; 544/305; 544/306; 544/309; 544/311; 544/312; 544/313; 544/314; 544/315; 544/316; 544/317; 544/318; 544/319; 544/321; 544/322; 544/323; 544/325; 544/326; 544/327; 544/329; 544/330; 544/332; 544/333; 544/334; 544/335; 546/194; 546/198; 546/199; 546/200; 546/201; 546/202; 546/205; 546/208; 546/209; 546/210; 546/211; 546/213; 546/230; 546/233; 546/234
[58] Field of Search ............... 514/248, 252, 256, 258, 514/259, 260, 269, 272, 274, 275, 318, 319, 320, 321, 322, 323, 324, 326, 331; 544/235, 237, 238, 253, 297, 298, 299, 301, 302, 303, 305, 306, 309, 311, 312, 313, 314, 315, 316, 317, 318, 319, 321, 322, 323, 325, 326, 327, 329, 330, 332, 333, 334, 335

[56] References Cited

U.S. PATENT DOCUMENTS 4,189,495 2/1980 Kaplan et al. .................. 424/274
4,357,337 11/1982 Dubroeucq et al. ............ 424/267

FOREIGN PATENT DOCUMENTS 0229391 7/1987 European Pat. Off. .
0296560 12/1988 European Pat. Off. .
1345872 2/1974 United Kingdom .

Primary Examiner—Richard L. Raymond
Assistant Examiner—Peter G. O'Sullivan
Attorney, Agent, or Firm—Wegner, Cantor, Mueller & Player

[57] ABSTRACT

The present invention relates to unsaturated carboxylic acid amide derivatives of the formula

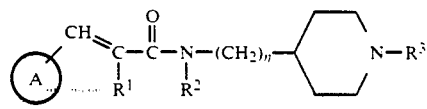

wherein ring A stands for an optionally substituted aromatic ring; $R^1$ stands for a hydrogen atom or an optionally substituted hydrocarbon residue or forms an optionally substituted carbocyclic ring with the adjacent group —CH=C— together with two carbon atoms constituting the ring A; $R^2$ stands for a hydrogen atom, an optionally substituted hydrocarbon residue or an optionally substituted acyl group; $R^3$ stands for an optionally substituted hydrocarbon residue; and n denotes an integer ranging from 2 to 6, and salts thereof, as well as the production thereof.

The compounds of the present invention act on the central nervous system of mammals and has a strong anti-cholinesterase activity, which can be used for the prophylaxis and therapy of, for example, senile dementia, Alzheimer's diseases, Huntington's chorea, et., and are useful as medicines.

22 Claims, No Drawings

PIPERIDINOALKYL DERIVATIVES OF CARBOXYLIC ACID AMIDES

This invention relates to novel unsaturated carboxylic acid amide derivatives useful as Pharmaceuticals, especially as agents for improving cerebral functions in senile dementia, Alzheimer's disease, etc.

With the increase of aged population, a variety of compounds having actions of improving cerebral functions have been suggested. Among them, physostigmine, an anticholinesterase agent, has been found to have an action of improving cerebral functions.

Physostigmine, however, has such drawbacks as a short duration of action and high toxicity.

The object of the present invention is to provide compounds with longer action and with lower toxicity, as compared with known compounds improving cerebral functions.

The present inventors succeeded in creating unsaturated carboxylic acid amide derivatives represented by the general formula (I):

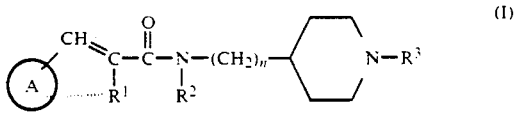

wherein ring A stands for an optionally substituted aromatic ring; $R^1$ stands for a hydrogen atom or an optionally substituted hydrocarbon group or forms an optionally substituted carbocyclic ring with the adjacent group —CH=C— together with two carbon atoms constituting the ring A; $R^2$ stands for a hydrogen atom, an optionally substituted hydrocarbon group or an optionally substituted acyl group; $R^3$ stands for an optionally substituted hydrocarbon group; and n denotes an integer ranging from 2 to 6, or salts thereof, and found that these compounds have a strong cholinesterase antagonizing action as well as a potent action of improving cerebral functions.

The present invention relates to compounds represented by the formula (I) or salts thereof, methods of preparing them and anticholinesterase agents containing them as well as agents containing them for improving cerebral functions.

In the above formula (I), examples of "hydrocarbon group" of "optionally substituted hydrocarbon group" represented by $R^1$, $R^2$ and $R^3$ include those in the form chain-like, cyclic, saturated or unsaturated group and combinations thereof. Examples of chain-like saturated hydrocarbon groups in chain form include straight-chain or branched alkyl groups of 1 to 11 carbon atoms (e.g. methyl, ethyl, n-propyl, i-propyl, n-butyl, i-butyl, tert-butyl, n-pentyl, n-hexyl).

Examples of chain-like unsaturated hydrocarbon groups in chain form include straight-chain or branched $C_{2-4}$ alkenyl e.g. vinyl, allyl, 2-butenyl, and $C_{2-4}$ alkynyl groups (e.g. propargyl, 2-butynyl).

Examples of cyclic saturated hydrocarbon groups include $C_{3-7}$ monocyclic cycloalkyl (e.g. cyclobutyl, cyclopentyl, cyclohexyl), and $C_{8-14}$ cross-linked cyclic saturated hydrocarbons, e.g. bicycloctyls such as bicyclo[3,2,1]oct-2-yl, bicyclononyls such as bicyclo[3,3,1]nonan-2-yl, and tricyclodecyls such as adamantan-1-yl. Cyclic unsaturated hydrocarbon groups include phenyl group, naphthyl group, etc.

Examples of substituents of these hydrocarbon groups include such groups as halogen atoms (e.g. chlorine, bromine, iodine), nitro, nitrile, hydroxy, $C_{1-4}$ alkoxy (e.g. methoxy, ethoxy, propoxy, butyloxy, isopropyloxy), $C_{1-4}$ alkylthio (e.g. methylthio, ethylthio, propylthio, isopropylthio, butylthio), amino, mono or di-$C_{1-4}$ alkyl substituted amino (e.g. methylamino, ethylamino, propylamino, dimethylamino, diethylamino), $C_{1-4}$ alkoxycarbonyl (e.g. methoxycarbonyl, ethoxycarbonyl, propoxycarbonyl, isobutoxycarbonyl), hydroxycarbonyl, $C_{1-6}$ alkylcarbonyl (e.g. methylcarbonyl, ethylcarbonyl, butylcarbonyl, cyclohexylcarbonyl), carbamoyl, mono- or di-$C_{1-4}$ alkyl substituted carbamoyl (e.g. methylcarbamoyl, ethylcarbamoyl, propylcarbamoyl, butylcarbamoyl, diethylcarbamoyl, dibutylcarbamoyl), phenyl, naphthyl, phenoxy, benzoyl, phenoxycarbonyl, phenyl $C_{1-4}$ alkylcarbamoyl and phenyl carbamoyl which may have 1 to 4 substituents and adamantan-1-yl. Substituents on the phenyl groups or naphthyl groups are exemplified by $C_{1-4}$ alkyl groups such as methyl, ethyl, propyl, butyl, isopropyl, etc. The phenyl groups can optionally have 1 to 4 substituents (substituents on the phenyl group are exemplified by $C_{1-4}$ alkyl group such as methyl, ethyl, propyl, butyl, isopropyl, etc., halogen such as chlorine, bromine, iodine, etc., hydroxy, benzyloxy, amino, mono- or di-$C_{1-4}$ alkyl-substituted amino, nitro, $C_{1-4}$ alkoxycarbonyl, etc.), halogen such as chlorine, bromine, iodine, hydroxy, benzyloxy, amino, mono- or di-$C_{1-4}$ alkyl-substituted amino, nitro, $C_{1-4}$ alkoxycarbonyl, etc.]

The preferred number of substituents of these hydrocarbon groups is 1 to 3.

The aromatic ring represented by the ring A includes aromatic cyclic compounds such as aromatic monocyclic hydrocarbon, aromatic condensed polycyclic hydrocarbon or aromatic heterocyclic ring. The aromatic monocyclic hydrocarbon is exemplified by benzene, and the aromatic condensed polycyclic hydrocarbon is exemplified by naphthalene, anthracene, etc. The aromatic heterocyclic ring includes 5- to 6-membered heterocyclic rings containing 1 to 4 hetero atoms selected from nitrogen atom, oxygen atom and sulfur atom. These aromatic heterocyclic rings are exemplified by thiophene, furan, pyrazole, thiazole, isothiazole, oxazole, isoxazole, imidazole, triazole, tetrazole, pyridine, pyrimidine, pyridazine, etc.

Among these heterocyclic rings, thiophene, furan, pyridine, etc., containing one hetero atom, are especially preferred.

In the above formula (I), $R^1$ may form a carbocyclic ring together with the adjacent group —CH=C— and two carbon atoms constituting the ring A. As such carbocyclic rings, 5-to 7-membered rings are especially desirable. As such carbon rings those having no aromaticity are especially desirable. The condensed ring formed by such a carbon ring as above and the ring A is exemplified by indene, 1,2-dihydronaphthalene, 6,7-dihydro-5H-benzocycloheptene, 5,6,7,8-tetra-hydrocyclooctene, 4,5-dihydrobenzo[b]thiophene, 4,5-dihydroisobenzofuran, 7,8-dihydroquinoline, 7,8-dihydroisoquinoline, etc. As substituents on these carbon rings are used $C_{1-4}$ alkyl groups such as methyl, ethyl, propyl, isopropyl, butyl, etc., halogen such as chlorine, bromine, iodine, hydroxyl group, $C_{1-4}$ alkyloxy groups such as methoxy, ethoxy, propyloxy, isopropyloxy, butyloxy, amino, mono- or di-$C_{1-4}$ alkyl-substituted amino such as methylamino, dimethylamino, etc., nitro, cyano, $C_{1-4}$ alkoxycarbonyl such as methoxycarbonyl, etc. The number of substituents on these carbon rings is preferably 1 to 3.

The acyl group represented by $R^2$ in the above formula (I) is exemplified by carboxylic acid acyl, carbamic acid acyl, sulfonic acid acyl, substituted hydroxycarboxylic acid acyl etc. The acyl groups may optionally have substituents.

Examples of the carboxylic acid acyl include $C_{1-6}$ alkylcarbonyl e.g. acetyl, propionyl, butyryl, valeryl, hexanoyl, isobutyryl, isovaleryl, etc., $C_{3-8}$ cycloalkylcarbonyl e.g. cyclopentanoyl, cyclohexanoyl, etc., $C_{3-8}$ cycloalkyl-$C_{1-6}$ alkylcarbonyl e.g. cyclopentylacetyl, etc., $C_{2-6}$ alkenyl or alkynylcarbonyl e.g. acryloyl, crotonyl, 2-pentenoyl, 4-pentynoyl, 2-hexenoyl, 3-hexenoyl, 2,4-hexadienoyl, etc., arylcarbonyl e.g. benzoyl, naphthoyl, etc.

As the carbamic acid acyl, use is made of, for example, carbamoyl, mono- or di-substituted carbamoyl. Examples of the mono- or di-substituted carbamoyl include mono- or di-$C_{1-4}$ alkylcarbamoyl such as methylcarbamoyl, ethylcarbamoyl, propylcarbamoyl, butylcarbamoyl, dimethylcarbamoyl, diethylcarbamoyl, dipropylcarbamoyl, etc., mono- or di-$C_{3-6}$ alkenyl carbamoyl such as allylcarbamoyl, 3-butenylcarbamoyl, 4-pentenylcarbamoyl, diallylcarbamoyl, etc., alkynylcarbamoyl or aromatic carbamoyl groups such as phenylcarbamoyl, naphthylcarbamoyl, diphenylcarbamoyl, etc.

Examples of the sulfonic acid acyl groups include inorganic sulfonyl groups such as sodium sulfonyl, $C_{1-6}$ alkylsulfonyl such as methylsulfonyl, ethylsulfonyl, propylsulfonyl, butylsulfonyl, etc., $C_{2-6}$ alkenyl- or alkynyl-sulfonyl such as allylsulfonyl, 2-methyl-2-propenylsulfonyl, etc., aromatic sulfonyl such as phenylsulfonyl, naphthalenesulfonyl, etc.

Examples of the substituted hydroxycarboxylic acid acyl groups include $C_{1-6}$ alkyloxycarbonyl such as methyloxycarbonyl, ethyloxycarbonyl, tert-butyloxycarbonyl, hexyloxycarbonyl, etc., $C_{3-8}$ cycloalkyloxycarbonyl such as cyclopentyloxycarbonyl, cyclohexyloxycarbonyl, etc., cycloalkyl-alkyloxycarbonyl such as cyclopentylmethyloxycarbonyl, etc., $C_{2-7}$ alkenylor alkynyl-oxycarbonyl such as allyloxycarbonyl, crotyloxycarbonyl, 2-penten-1-oxycarbonyl, etc., or aromatic or aromatic aliphatic hydroxycarbonyl such as phenyloxycarbonyl, or phenyl-$C_{1-2}$ alkoxycarbonyl such as benzyloxycarbonyl, etc.

As the substituents, these substituents can be groups exemplified by the above-mentioned substituents of hydrocarbon residues. The preferable number of such substituents is 1 to 3.

Referring to the stereochemistry at the site of the double bond shown by —CH=C— of the above formula (I), either the E-isomer or Z-isomer or a mixture thereof may be usable.

As the substituents which the ring A in the above formula (I) may optionally have (one of the substituents on the ring A is sometimes shown as X), there can be used, for example, a $C_{1-4}$ alkyl (e.g. methyl, ethyl, propyl, butyl, etc.), a halogen atom (e.g. chlorine, bromine, iodine), nitro, cyano, hydroxy, a $C_{1-4}$ alkoxy (e.g. methoxy, ethoxy, propyloxy, butyloxy, isopropyloxy, etc.), a $C_{1-4}$ alkylthio (e.g. methylthio, ethylthio propylthio, isopropylthio, butylthio, etc.), amino, a mono- or di-$C_{1-4}$ alkyl-substituted amino (e.g. methylamino, ethylamino, propylamino, dimethylamino, diethylamino, etc.), $C_{1-4}$ alkylcarbonylamino (e.g. acetylamino, propionylamino, butyrylamino, etc.), $C_{1-4}$ alkylsulfonylamino e.g. methylsulfonylamino, ethylsulfonylamino, propylsulfonylamino, etc.), $C_{1-4}$ alkoxycarbonyl (e.g. methoxycarbonyl, ethoxycarbonyl, propoxycarbonyl, isobutoxycarbonyl, etc.), hydroxycarbonyl, $C_{1-6}$ alkylcarbonyl (e.g. methylcarbonyl, ethylcarbonyl, butylcarbonyl, cyclohexylcarbonyl, etc.), carbamoyl, mono- or di-$C_{1-4}$ alkyl-substituted carbamoyl (e.g. methylcarbamoyl, ethylcarbamoyl, propylcarbamoyl, butylcarbamoyl, diethylcarbamoyl, dibutylcarbamoyl, etc.), $C_{1-6}$ alkylsulfonyl (e.g. methylsulfonyl, ethylsulfonyl, propylsulfonyl, cyclopentylsulfonyl, cyclohexylsulfonyl, etc.), phenyl, phenoxy, benzoyl, phenoxycarbonyl, phenyl $C_{1-4}$ alkylcarbamoyl, phenylcarbamoyl, phenyl $C_{1-4}$ alkylcarbonylamino, benzoylamino, phenyl-$C_{1-4}$ alkylsulfonyl, phenylsulfonyl, phenyl $C_{1-4}$ alkylsulfonylamine and phenylsulfonylamino group, which may have 1 to 4 further substituents. The phenyl groups in these substituents can be further substituted by $C_{1-4}$ alkyl groups such as methyl, ethyl, propyl, butyl, isopropyl, etc., halogen such as chlorine, bromine, iodine, hydroxy, benzyloxy, amino, mono- or di-$C_{1-4}$ alkyl-substituted amino such as methylamino, dimethylamino, etc., nitro, $C_{1-4}$ alkoxycarboxy groups. The number of substituents on the ring A is preferably 1 to 3. Ring A is preferably unsubstituted or has one or two of the above substituents.

When $R^1$ forms an optionally substituted carbocyclic ring with the adjacent group —CH=C— together with two carbon atoms constituting the ring A, compound (1) can be represented by the formula (I'):

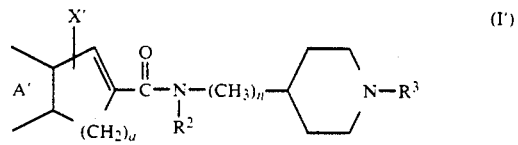

wherein A' is a ring defined in the same way as ring A above; X' is hydrogen, $C_{1-4}$ alkyl, halogen, hydroxy, $C_{1-4}$ alkoxy, amino, mono- or di-$C_{1-4}$ alkylamino, cyano or $C_{1-4}$ alkoxycarbonyl etc.; a is an integer from 1 to 3, and other the symbols are defiend above.

Referring to preferable embodiments of the compounds shown by the above formula (I), as the ring A, benzene, pyridine, furan and thiophene can be used, and benzene and pyridine are especially preferable.

Preferable examples of $R^1$ include a hydrogen atom, $C_{1-6}$ alkyl group such as methyl, ethyl, propyl, etc., a substituted or unsubstituted phenyl group, or $R^1$ can also preferably be a group forming 1,2-dihydronaphthalene or 6,7-dihydro-5H-benzocycloheptane together with the adjacent group —CH=C— and two carbon atoms of the ring A. Especially preferred $R^1$ is a hydrogen atom or phenyl or where 6,7-dihydro-5H-benzocycloheptene is formed in combination with the adjacent double bonded group —CH=C— and the ring A.

Preferable examples of $R^2$ include a hydrogen atom, $C_{1-6}$ alkyl such as methyl, ethyl, propyl, etc., optionally substituted phenyl, $C_{1-6}$ alkylcarbonyl such as acetyl, propionyl, butyryl, etc. or arylcarbonyl such as benzoyl, especially hydrogen atom, $C_{1-6}$ alkylcarbonyl or benzoyl.

As $R^3$, an optionally $C_{1-3}$ alkyl substituted aromatic hydrocarbon, e.g. phenyl, naphthyl or phenyl-$C_{1-3}$ alkyl can be used, benzyl is especially preferred.

Preferable examples of the substituents (X) on the ring A include a $C_{1-4}$ alkyl group such as methyl, ethyl, propyl, etc., halogen atom such as chlorine, bromine, etc., nitro, cyano, a $C_{1-4}$ alkoxy group such as methoxy, ethoxy, propyloxy, etc., an optionally substituted phenoxy $C_{1-4}$ alkylcarbonylamino such as acetylamino, propionylamino, $C_{1-4}$ alkylsulfonylamino such as methylsulfonylamino, ethylsulfonylamino, etc., phenyl $C_{1-4}$ alkylsulfonylamino such as benzylsulfonylamino, etc., optionally substituted phenylsulfonylamino, $C_{1-4}$ alkylcarbonyl such as acetyl, propionyl, butyryl, etc., $C_{1-4}$ alkoxycarbonyl such as methoxycarbonyl, ethoxycarbonyl, butoxycarbonyl, etc., optionally substituted phenoxycarbonyl, optionally substituted benzoyl, carbamoyl, mono- or di-$C_{1-4}$ alkyl-substituted carbamoyl such as methylcarbamoyl, ethylcarbamoyl, butylcarbamoyl, etc., optionally substituted phenylcarbamoyl, optionally substituted $C_{1-6}$ alkylthio such as methylthio, ethylthio, propylthio, etc., optionally substituted phenyl-$C_{1-4}$ alkylthio such as benzylthio, phenethylthio, etc., optionally substituted $C_{1-6}$ alkylsulfinyl such as metylsulfinyl, ethylsulfinyl, propylsulfinyl, etc., optionally substituted phenyl-$C_{1-4}$ alkylsulfinyl such as benzylsulfinyl, phenethylsulfinyl, etc., $C_{1-6}$ alkylsulfonyl such as methylsulfonyl, propylsulfonyl, cyclohexylsulfonyl, etc., optionally substituted phenyl-$C_{1-4}$ alkylsulfonyl, phenyl-$C_{1-4}$ alkyl such as optionally substituted phenylsulfonyl, optionally substituted phenyl, phenyl-$C_{1-4}$ alkyl such as optionally substituted benzyl, etc. Among them, $C_{1-4}$ alkyl, halogen nitro, cyano, acetylamino, $C_{1-4}$ alkoxy, optionally substituted phenyl, optionally substituted benzyl, optionally substituted benzoyl, optionally substituted benzoylamino, optionally substituted $C_{1-6}$ alkylsulfonyl, optionally substituted benzylsulfonyl, optionally substituted phenylsulfonylamino, optionally substituted benzylsulfonylamino, optionally substituted phenylcarbamoyl. methoxycarbonyl, diethoxycarbonyl, etc. are especially preferable.

The substituent X on ring A which contains a phenyl group therein is referred to herein also as group Q. Thus, group Q includes a phenyl, benzyl, benzoyl, benzoylamino, benzylsulfonyl, phenylsulfonylamino, benzylsulfonylamino, or phenylcarbamoyl etc. The group Q may be optionally substituted with 1 to 3 of $C_{1-4}$ alkyl, phenyl, halogen, hydroxy, benzyloxy, amino, mono- or di-$C_{1-4}$ alkylamino, nitro or $C_{1-4}$ alkoxycarbonyl etc.

As X, electron attractive groups are especially preferable among the above-mentioned groups.

The ring having no substituent is also preferable.

As n are preferable 2,3 and 4.

Especially preferred are compounds (I) wherein the ring A is benzene or pyridine; $R^1$ is a hydrogen atom, methyl or phenyl group or forms 6,7-dihydro-5H-benzocycloheptene or 1,2-dihydronaphthalene together with the adjacent group —CH=C— and the ring A; R2 is an acetyl or propionyl group, $R^3$ is a benzyl group; n is 2, 3 or 4; and the ring A is unsubstituted or substituted with a nitro group or acylamino group.

The compound (I) of the present invention may form an acid addition salt, especially a physiologically acceptable acid addition salt. As these salts, mention is made of, for example, salts with an inorganic acid (e.g. hydrochloric acid, nitric acid, phosphoric acid, hydrobromic acid, sulfuric acid) or with an organic acid (e.g. acetic acid, formic acid, propionic acid, fumaric acid, maleic acid, succinic acid, tartaric acid, citric acid, maleic acid, ascorbic acid, oxalic acid, benzoic acid, methansulfonic acid, benzenesulfonic acid). When the object compound (I) has an acid group such as —COOH, the object compound (I) may form a salt with an inorganic base such as sodium, potassium, calcium, magnesium, ammonia, etc. or an organic base such as trimethylamine, etc.

In the following, the method of producing the object compound (I) is described.

The following explanation is applicable not only to the basic compound (I) per se [including a compound usable as the starting compound for preparing another compound included in the definition of compound (I)], but also the salts thereof mentioned above, and, in the following explanation, these compounds are simply referred to as compound (I).

The compound (I) can be produced by allowing, for example, a compound represented by the formula (II):

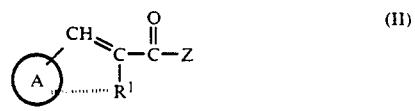

wherein Z stands for a hydroxyl group or a reactive group of carboxylic acid, and other symbols are of the same meaning as defined above, to react with, for example, a compound represented by the formula (III):

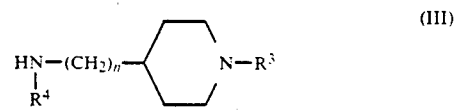

wherein $R^4$ is the same as $R^2$ except in the case of optionally substituted acyl, namely, a hydrogen atom or an optionally substituted hydrocarbon residue; $R^3$ and n are of the same meaning as defined above, or a salt thereof.

As the reactive group of a carboxylic acid represented by Z, mention is made of halogen (e.g. chlorine, bromine, iodine), a lower($C_{1-4}$) alkoxy (e.g. methoxy, ethoxy, propoxy, butoxy) and N-hydroxydiacylimidoester (e.g. N-hydroxysuccinic imidoester, N-hydroxyphthalimidoester, N-hydroxy-5-norbornen-2,3-dicarboxyimidoester), etc.

These reactions are carried out usually in an organic solvent such as hydrocarbon (e.g. pentane, hexane, benzene, toluene), halogenated hydrocarbon (e.g. dichloromethane, chloroform, dichloroethane, carbon tetrachloride), ether (e.g. ethylether, tetrahydrofuran, dioxane, dimethoxyethane), ester (e.g. ethyl acetate, butyl acetate, methyl propionate), amide (e.g. dimethylformamide, dimethylacetamide, hexamethylphosphonotriamide), dimethylsulfoxide, etc., under cooling (−10° C. to 10° C.), at room temperatures (11° C. to 40° C.), or under heating (41° C. to 120° C.), and the reaction time ranges usually from 10 minutes to 12 hours. The amount of the compound (III) is preferably 1.0 to 3.0 equivalents relative to the compound (II). This reaction can be carried out, when desired, for example in the case where Z is hydroxy, in the presence of an acid activating agent such as carbonyldiimidazole, dicyclohexylcarbodiimide, diethyl cyanophosphonate, diphenylphosphorylazide, etc., and, in the case where Z is halogen or lower alkoxy, in the presence of an organic base such as pyridine, 4-dimethylaminopyridine, triethylamine, diisopropylamine, triethylenediamine, tetramethylethylenediamine, etc. or in the presence of an inorganic base such as sodium hydrogen carbonate, potassium hydrogen carbonate, lithium hydrogen carbonate, potassium carbonate, sodium carbonate, lithium carbonate, lithium hydroxide, potassium hydroxide, sodium hydroxide, sodium hydride, etc.

In the case where Z is N-hydroxydiacylimidoester, the reaction is carried out in a solvent, for example, dichloromethane, tetrahydrofuran, dioxane, chloroform, dimethylformamide, acetonitrile, water, etc. This reaction is carried out, when necessary, in the presence of an organic or inorganic base. The reaction temperature ranges usually from $-10°$ C. to $110°$ C., preferably from $0°$ C. to $30°$ C., and the reaction time ranges usually from 5 minutes to 12 hours, preferably from 30 minutes to two hours.

A compound of the formula (II) wherein Z is hydroxy [hereinafter abbreviated as compound (II: Z=hydroxy)], i.e. a free carboxylic acid, can be easily prepared by a per se conventional means, for example, by subjecting the compound (II: Z=lower alkoxy), i.e. the ester compound, to hydrolysis with an alkali metal hydroxide (e.g. potassium hydroxide, lithium hydroxide, sodium hydroxide), an alkali metal carbonate (e.g. potassium carbonate, sodium carbonate, lithium carbonate), mineral acid (e.g. hydrochloric acid, sulfuric acid, nitric acid, phosphoric acid, perchloric acid, hydroiodic acid), an organic acid (e.g. acetic acid, propionic acid, trifluoroacetic acid, monochloroacetic acid, trichloroacetic acid, methanesulfonic acid, ethanesulfonic acid, p-toluenesulfonic acid). For the hydrolysis, any conventional solvent can be employed, for example, water, lower($C_{1-4}$) alkanols (e.g. methanol, ethanol, propanol, butanol), dioxane, tetrahydrofuran, dimethylformamide, etc. are preferable. The reaction temperature ranges usually from about $-10°$ C. to about $120°$ C., preferably from $0°$ C. to $80°$ C. The reaction time ranges usually from 10 minutes to 24 hours, preferably from 30 minutes to 6 hours.

The compound (II: Z=halogen) can be prepared by a per se conventional means, for example, by subjecting carboxylic acid to halogenation using a halogenating agent (e.g. phosphorus oxychloride, phosphorus oxybromide, phosphorus pentachloride, phosphorus pentabromide, thionyl chloride, thionyl bromide, sulfuryl chloride, oxalyl chloride, cyanuric acid chloride, boron tribromide, hydrogen iodide). As acid halides to be obtained by the halogenation are mentioned, for example, acid chloride, acid bromide, acid fluoride and acid iodide, especially acid chloride and acid bromide are preferable.

The above-mentioned halogenation is carried out in the absence of solvent or in a conventional solvent. Preferable solvents are, for example, inactive ones such as chloroform, dichloromethane, dichloroethane, benzene, toluene, etc.

The compound (II: Z=hydroxydiacylimidoester) can be prepared by, in a per se conventional manner, allowing the compound (II: Z=hydroxy) to react with an N-hydroxydicarboxylic acid imide (e.g. N-hydroxysuccinic acid imide, N-hydroxyphthalic acid imide, N-hydroxy-5-norbornen-2,3-dicarboxyimide) in the presence of dicyclohexylcarbodiimide. This reaction is carried out in a conventional solvent (e.g. tetrahydrofuran, dioxane, dimethylformamide, acetonitrile, water), and the compound (II: Z=N-hydroxydiacylimidoester) can be fed to the subsequent reaction without isolation thereof.

The compound (II) usable as the starting material can be prepared by a known method or a method analogous thereto. The compound (III) can also be prepared in accordance with a known method or a method analogous thereto.

Among the compounds (III), for example, the compound (III: $R^3=CH_3Ph$, $R^4=H$, n=2) (wherein Ph stands for phenyl group, hereinafter the same abbreviation will be applied.) is a known compound, which is disclosed in Synthesis, 388 (1983).

The compound (III) can be prepared by a per se known method by using a known compound represented by the formula(III'):

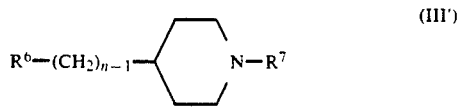

wherein $R^6=CO_2C_2H_5$, $R^7=CO_2CH_2Ph$, and n=an integer of 2 to 6. For example, the compound (III': $R^6=CO_2C_2H_5$, $R^7=CO_2CH_2Ph$, n=integer of 2 to 6) is subjected to catalytic reduction by a conventional method or is treated with an acid to give a compound (III': $R^6$ and n are of the same meaning as defined above, $R^7=H$), to which was then introduced a hydrocarbon residue by a conventional method to give a compound-[III': $R^6$ and n are of the same meaning as above, $R^7=R^3$ ($R^3$ is of the same meaning as above)], then the ester group of $R^6$ is subjected to amidation directly by a conventional means or amidation after converting the ester group of $R^6$ into a carboxyl group to thereby obtain a compound [III': $R^6=CONHR^4$, $R^7=R^3$ ($R^3$ and n are of the same meaning as defined above)], followed by subjecting the compound to reduction with lithium aluminium hydride by per se conventional means to afford the compound (III).

The above-mentioned known compound, the starting compound, (III':$R^6=CO_2CH_2H_5$, $R^7=CO_2CH_2Ph$, n=an integer of 2 to 6) is that disclosed in Japanese Patent Publication (laid open) 99476/1981 and Chem. Pharm. Bull. 34. 3747(1986).

Among the object compounds (I) of the present invention, a compound (I) in which $R^5=R^2$ (except for the case of $R^5$=hydrogen, wherein $R^5$ is an optionally substituted hydrocarbon residue or acyl group) can also be prepared by introducing hydrocarbon residue into the object compound of this invention (I: $R^2=H$) or by subjecting the said compound to acylation. For example, the above compound (I: $R^2=R^5$) can be prepared also by allowing a compound (I: $R^2=H$) to react with a compound represented by the formula (IV): $R^5$-Y (wherein $R^5$ is defined as above; when $R^5$ is an optionally substituted hydrocarbon residue, Y stands for halogen, and, when $R^5$ is an optionally substituted acyl group, Y stands for hydroxy, $OR^5$ or a reactive group of carboxylic acid) by a per se known method.

In the reaction of the compound (I: $R^2=H$) with a compound (IV], use of a solvent is not always required, and, when required, use of an organic solvent such as hydrocarbon (e.g. pentane, hexane, benzene, toluene), halogenated hydrocarbon (e.g. dichloromethane, chloroform, dichloroethane, carbon tetrachloride), ether (e.g. ethyl ether, tetrahydrofuran, dioxane, dimethoxyethane), amide (e.g. dimethylformamide, hexamethylphosphonotriamide), dimethylsulfoxide, etc. is preferable. The reaction is carried out at temperatures ranging from −10° C. to 200° C., preferably from 0° C. to 120° C. The reaction time ranges usually from 5 minutes to 12 hours, preferably from 10 minutes to 6 hours. The amount of the above-mentioned compound (IV) is usually equimolar or in an excess relative to the compound (I: $R^2=H$), preferably 1.1 to 20.0 times as much per mole. When $R^5$ is an optionally substituted hydrocarbon residue and Y is halogen, the reaction is carried out in the presence of, for example, an organic base such as pyridine, 4-dimethylaminopyridine, triethylamine, diisopropylamine, triethylenediamine, tetramethylethylenediamine, etc. or an inorganic base such as sodium hydride, metallic sodium, potassium amide, sodium hydrogen carbonate, potassium hydrogen carbonate, sodium carbonate, potassium carbonate, lithium hydroxide, potassium hydroxide, sodium hydroxide,etc. The amount of these bases is generally equimolar to excess relative to the compound (II: $R^2=H$), preferably 1.1 to 5 times as much mol.

And, Examples of the reactive groups of carboxylic acid represented by Y when $R^5$ stands for an acyl group include halogen (e.g. chlorine, bromine, iodine), lower($C_{1-4}$) alkoxy (e.g. methoxy, ethoxy, propoxy, butoxy) and N-hydroxydiacylimidoester (e.g. N-hydroxysuccinic acid imidoester, N-hydroxyphthalic acid imidoester, N-hydroxy-5-norbornene-2,3-dicarboxyimidoester), etc.

And, the reaction of the compound (I: $R^2=H$) with a compound (IV), when $R^5$ is an acyl group, can be carried out, if desired, when Y is hydroxy, in the presence of an acid-activating agent such as carbonyldiimidazole, dicyclohexylcarbodiimide, diethyl cyanophosphate, diphenylphosphorylazide, etc., when Y is $OR^5$, in the presence of a mineral acid such as hydrochloric acid, hydrobromic acid, sulfuric acid, nitric acid, phosphoric acid, etc., an organic acid such as acetic acid, formic acid, propionic acid, methanesulfonic acid, p-toluenesulfonic acid, etc. or an acyl halogenide whose acyl group is the same as $R^5$, and, when Y is halogen or a lower alkoxy, in the presence of an organic base such as pyridine, 4-dimethylaminopyridine, triethylamine, diisopropylamine, triethylenediamine, tetramethylethylenediamine, etc. or an inorganic base such as sodium hydrogen carbonate, potassium hydrogen carbonate, lithium hydrogen carbonate, lithium hydroxide, potassium hydroxide, sodium hydroxide, etc.

Further, when Y is a N-hydroxydiacylimido ester, the reaction is carried out in a solvent, for example, preferably dichloromethane, tetrahydrofuran, dioxane, chloroform, dimethylformamide, acetonitrile, water, etc. This reaction can be carried out, upon desire, in the presence of an organic or an inorganic base mentioned above referring to the case where Y is halogen or lower alkoxy.

When the reaction is carried out in the presence of the above-mentioned acid-activating agent, acid, halide and base, the amount of these agents ranges generally from equimolar. to excess relative to the compound (I: $R^2=H$), preferably in 1.1 to 5 times molar excess.

And, among the object compounds (I) of the present invention, the compound (I: $X=NH_2$) can also be prepared by subjecting also the object compound of the present invention (I: $X=NO_2$) or a salt thereof. The reduction can be conducted by a per se known method, for example those disclosed in J. Am. Chem. Soc., 49 1093(1927) or Ber., 76, 1011(1943) or an equivalent.

This reaction can be carried out, for example, by conducting a catalytic reduction in hydrogen streams, in the presence of a catalyst (e.g. palladium-carbon, platinum dioxide) at normal temperatures under normal pressure. As the solvent, use is made of, for example, methanol, ethanol, water, dimethylformamide, dioxane, etc., but any other solvents can be used so long as they do not inhibit this reaction. This reaction can be carried out, when desired, in the presence of a mineral acid such as hydrochloric acid, hydrobromic acid, sulfuric acid, etc. or an organic acid such as acetic acid, formic acid, propionic acid, oxalic acid, etc.

A compound (I), wherein X stands for an acylamino group (e.g. acetylamino, benzoylamino, benzenesulfonylamino) can be prepared by subjecting a compound (I: $X=NH_2$) to acylation. This acylation can be carried out by allowing the compound (I:$X=NH_2$) to react with an acylating agent, for example, an acid (e.g. acetic acid, propionic acid, benzoic acid, benzenesulfonic acid, p-toluenesulfonic acid), $C_{1-4}$ alkyl ester of an acid (e.g. methyl acetate, ethyl propionate, methyl benzenesulfonate), an acid halogenide (e.g. acetyl chloride, acetyl bromide, p-toluenesulfonic acid chloride, benzenesulfonyl chloride), an acid anhydride (acetic anhydride, propionic anhydride, benzoic anhydride) or N-hydroxydiacylimido ester of an acid (e.g. N-acetyloxysuccinimide, N-benzoyloxyphthalimide, N-acetyloxy-5-norbornene-2,3-dicarboxyimide), etc.

These reactions can usually be carried out in an organic solvent such as hydrocarbon (e.g. pentane, hexane, benzene, toluene), halogenated hydrocarbon (e.g. dichloromethane, chloroform, dichloroethane, carbon tetrachloride), ether (e.g. ethyl ether, tetrahydrofuran, dioxane, dimethoxyethane), ester (e.g. ethyl acetate, butyl acetate, methyl propionate), amide (e.g. dimethylformamide, dimethylacetamide, hexamethylphosphonotriamide), dimethylsulfoxide, etc., under cooling (−10° C. to 10° C.), at room temperatures (11° C. to 40° C.) or under heating (41° C. to 120° C.), and the reaction time ranges from 10 minutes to 12 hours. The amount of the above-mentioned acylating agents ranges preferably from 1.0 to 3.0 equivalents relative to the compound (I: $X=NH_2$). Further, this reaction can be carried out, if desired, when the acylating agent is an acid, in the presence of, for example, an acid-activating agent such as carbonyldiimidazole, dicyclohexylcarbodiimide, diethyl cyanophosphate, diphenylphosphorylazide, etc., and, if the acylating agent is $C_{1-4}$ alkyl ester of an acid or an acid halide, in the presence of an organic base such as pyridine, 4-dimethylaminopyridine, triethylamine, diisopropylamine, triethyleneamine, tetramethylethylenediamine, etc. or in the presence of an inorganic base such as sodium hydrogen carbonate, potassium hydrogen carbonate, lithium carbonate, lithium hydroxide, potassium hydroxide, sodium hydroxide, etc., and, if the acylating agent is an acid anhydride, in the presence of a mineral acid such as hydrochloric acid, hydrobromic acid, sulfuric acid, nitric acid, phosphoric acid, etc. or an organic acid such as acetic acid, formic acid, propionic acid, methanesulfonic acid, p-toluenesulfonic acid, etc.

Further, if the acylating agent is an N-hydroxydiacylimido ester, the acylation is carried out preferably in the presence of a solvent such as dichloromethane, tetrahydrofuran, dioxane, chloroform, dimethylformamide, acetonitrile, water, etc. This reaction can be carried out, when desired, in the presence of such an organic or inorganic base as mentioned above. The reaction temperature ranges, usually, from −10° C. to 110° C., preferably from 0° C. to 30° C., and the reaction time ranges, usually, from 5 minutes to 12 hours, preferably from 30 minutes to 2 hours.

The compound (I) of the present invention acts on the central nervous system of mammals, has a strong anticholinesterase activity and shows an excellent antiamnesic action against various types of induction of amnesia in humans and animals such as mice.

The compound (I) of the present invention has, as compared with physostigmine, such characteristic features as showing a very good separability of the action on the central nerves from that on peripheral nerves, being accompanied with no or very slight actions on peripheral nerves causing convulsion, salivation, diarrhea, in the dosage showing antiamnestic action. The compound (I) has prolonged action and is of low toxicity; it is a remarkably effective by oral administration.

Therefore, the present compounds are useful in agents for improving cerebral functions in a mammal including human beings.

The diseases to which the compounds of the present invention can be effectively applied are senile dementia, Alzheimer's disease, Huntington's chorea, hyperkinesis, mania, etc., and the compounds can be used for the prophylaxis or therapy of these diseases.

The compounds of the present invention can be administered orally or non-orally to mammals including man in various dosage forms such as tablets, granules, capsules, injections, suppositories and so forth. The dose varies with the kinds of deseases, symptoms, etc. Generally, however, in the case of oral administration, the daily dose ranges from 0.001 mg to 100 mg, preferably from 0.01 mg to 10 mg.

The following examples, reference examples, formulation examples and experimental examples are intended to illustrate the present invention in further detail and should by no means be construed as limiting the scope of the present invention.

The elution in column chromatography in the examples and reference examples were conducted, unless otherwise specified, using the technique of Thin Layer Chromatography (TLC). The eluate fractions containing the object compound were confirmed and collected by employing, as a supplemental means of detection, the procedure which comprises spraying 48% HBr onto the spot on the TLC plate, hydrolyzing by heating, then spraying thereon a ninhydrin reagent, and heating again to cause change of the color to red to reddish purple. Unless otherwise specified, the silica gel used for the column was Kiesel-gel 60 (70 to 230 mesh) manufactured by E. Merck AG.

The term "room temperatures" usually ranges from about 5° C. to 40° C.

Unless otherise specified, % means weight percentage.

EXAMPLE 1

(E)-3-Phenyl-N-[2-(1-benzylpiperidin-4-yl)ethyl]-2propenamide.hydrochloride

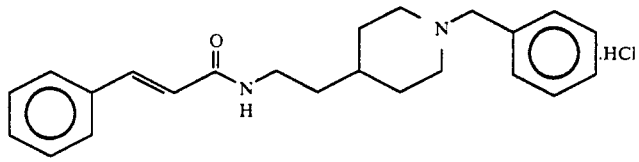

To a dimethylformamide solution (20 ml) containing (E)-cinnamic acid (1.05 g), 4-(2-aminoethyl)-1-benzylpiperidine.dihydrochloride (1.8 g) and triethylamine (1.0 ml) was added, under ice-cooling, diethyl cyanophosphonate (1.7 g). The mixture was stirred for one hour under ice-cooling, and there was added water (100 ml). The mixture was subjected to extraction with dichloromethane. The dichloromethane solution was dried over anhydrous sodium sulfate, then the solvent was distilled off under reduced pressure The oily residue was subjected to a silica gel column chromatography [developing solvent : ethyl acetate - methanol = 20 : 1(V/V)]. The solvent of the solution containing the object product was distilled off. To the residue was added an ethanolic solution (2.4 ml) of 3N hydrochloric acid, then the solvent was distilled off. The residual solid was recrystallized from ethanol-ether [5:1(V/V)]to give colorless crystals (1.2 g) m.p. 125° to 127° C.

Elemental Analysis for $C_{23}H_{28}N_2O \cdot HCl$ :
Calcd : C 71.76 H 7.59 N 7.28
Found : C 71.62 H 7.49 N 7.01

EXAMPLE 2

(E)-3-Phenyl-N-methyl-N-[2-(1-benzylpiperidin-4-yl)ethyl]-2-propenamide.hydrochloride

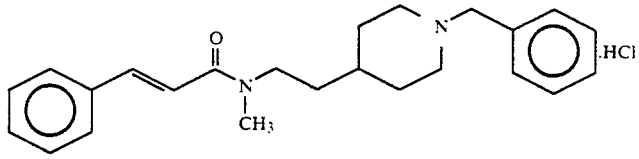

To a dimethylformamide solution (5 ml) of (E)-3-phenyl-N-[2-(1-benzylpiperidin-4-yl)ethyl]-2-propenamide.hydrochloride (0.6 g) obtained in Example 1 was gradually added sodium hydride (80 mg) at room temperature and the mixture was stirred at 60° C. for 30 minutes. The reaction mixture was cooled on an ice-bath and there was added methyl iodide (0.21 g), followed by stirring at room temperature for one hour. To the resultant mixture was added water and the mixture was subjected to extraction with dichloromethane. The dichloromethane solution was washed with water and dried over anhydrous sodium sulfate, then the solvent was distilled off. The oily residue was subjected to a silica gel column chromatography [developing solvent : ethyl acetate - methanol = 10 : 1(V/V)]. Then the solvent of the solution containing the object compound was distilled off. To the residue was added an ethanolic solution (0.5 ml) of 3N hydrogen chloride, followed by distilling off the solvent to obtain an amorphous powder (0.2 g).

Elemental Analysis for $C_{24}H_{30}N_2O.HCl$ :
Calcd. : C 72.25 H 7.83 N 7.02
Found : C 72.01 H 7.79 N 6.95

EXAMPLE 3

(E)-3-Phenyl-N-acetyl-N-[2-(1-benzylpiperidin-4yl)ethyl]-2-propenamide.hydrochloride

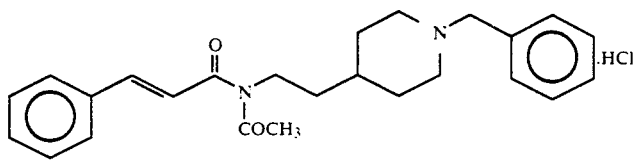

(A) A mixture of (E)3-phenyl-N-[2-(1-benzylpiperidin-4yl)ethyl]-2-propenamide.hydrochloride (0.5 g), acetic anhydride (2.5 ml) and a catalytic amount of p-toluenesulfonic acid.monohydrate was stirred at 80° C. for 6 hours. The reaction mixture was left standing for cooling, after there was added water. To the mixture was added 10% NaOH to render the pH to about 9 to 10, followed by extraction with dichloromethane. The dichloromethane solution was washed with water and dried over anhydrous sodium sulfate, followed by distilling off the solvent. The oily residue was subjected to a silica gel column chromatography (developing solvent : ethyl acetate). The solvent of the solution containing the object compound was distilled off. To the residue was added an ethanol solution (0.44 ml) of 3N hydrogen chloride, and the solvent was distilled off to obtain a hygroscopic amorphous powder (0.45 g).

Elemental Analysis for $C_{25}H_{30}N_2O_2.HCl$ :
Calcd. : C 70.32 H 7.32 N 6.56
Found : C 70.18 H 7.29 N 6.41

(B) A pyridine solution (5 ml) of (E)-3-phenyl-N-[2-(1-benzylpiperidin-4-yl)ethyl]-2-propenamide. hydrochloride (0.25 g) and acetyl chloride (0.3 ml) was stirred at 60° C. for 2 hours. Water was added to the reaction mixture after being left standing for cooling; the mixture was dried over anhydrous sodium sulfate. The solvent was distilled off. The oily residue was subjected to silica gel column chromatography (developing solvent : ethyl acetate). The solvent of the solution containing the object compound was distilled off. To the residue was added an ethanol solution of 3N hydrogen chloride. The solvent was then distilled off to obtain hydroscopic amorphous powder (0.16 g).

Elemental Analysis for $C_{25}H_{30}N_2O_2.HCl$ :
Calcd. : C 70.32 H 7.32 N 6.56
Found : C 70.26 H 7.13 N 6.48

EXAMPLE 4

By the procedure of Example 1, compounds as set forth in Table 1 were obtained.

TABLE 1

| Compound No. | A | R¹ | n | m.p. (°C.) | Molecular Formula | Elemental Analysis Calcd. (Found) C | H | N |
|---|---|---|---|---|---|---|---|---|
| 1 | phenyl | CH₃ | 2 | amorphous | $C_{24}H_{30}N_2O.HCl$ | 72.25 (72.18 | 7.83 7.74 | 7.02 6.98) |
| 2 | phenyl | $C_6H_5$ | 2 | amorphous | $C_{29}H_{32}N_2O.HCl$ | 75.55 (75.48 | 7.21 7.11 | 6.08 6.00) |
| 3 | pyridyl | H | 2 | 113–115 | $C_{29}H_{27}N_3O$ | 75.61 (75.52 | 7.79 7.72 | 12.02 11.96) |
| 4 | furyl | H | 2 | 180–183 | $C_{21}H_{26}N_2O_2.HCl$ | 67.28 (67.27 | 7.26 7.11 | 7.47 7.39) |
| 5 | thienyl | H | 2 | 89–92 | $C_{21}H_{26}N_2OS.HCl$ | 64.51 (64.44 | 6.96 6.93 | 7.17 7.01) |

TABLE 1-continued

Structure: A-CH=C(R¹)-C(=O)-NH-(CH$_2$)$_n$-[piperidine]-NCH$_2$-phenyl

| Compound No. | A | R¹ | n | m.p. (°C.) | Molecular Formula | Elemental Analysis Calcd. (Found) | | |
|---|---|---|---|---|---|---|---|---|
| | | | | | | C | H | N |
| 6 | 3,4-(CH$_3$O)$_2$-phenyl | H | 2 | amorphous | C$_{25}$H$_{32}$N$_2$O$_3$·HCl | 67.48 (67.32 | 7.47 7.45 | 6.30 6.27) |
| 7 | 6,7-(CH$_3$O)$_2$-3,4-dihydronaphthalenyl | | 2 | amorphous | C$_{27}$H$_{34}$N$_2$O$_3$·HCl | 68.85 (68.81 | 7.49 7.45 | 5.95 5.86) |
| 8 | 4-O$_2$N-phenyl | H | 2 | amorphous | C$_{23}$H$_{27}$N$_3$O$_3$·HCl | 64.25 (64.11 | 6.56 6.42 | 9.77 9.61) |
| 9 | 4-NC-phenyl | H | 2 | amorphous | C$_{24}$H$_{27}$N$_3$O·HCl | 70.32 (70.14 | 6.88 6.83 | 10.25 10.01) |
| 10 | 4-CH$_3$O$_2$S-phenyl | H | 2 | 158-160 | C$_{24}$H$_{30}$N$_2$O$_3$S | 67.58 (67.39 | 7.09 6.98 | 6.57 6.43) |
| 11 | 4-CH$_3$-phenyl | H | 2 | amorphous | C$_{24}$H$_{30}$N$_2$O·HCl | 72.25 (72.06 | 7.83 7.77 | 7.02 6.93) |
| 12 | 4-Cl-phenyl | H | 2 | 108-110 | C$_{23}$H$_{27}$ClN$_2$O | 72.14 (72.03 | 7.11 6.99 | 7.32 7.03) |

EXAMPLE 5

By a procedure similar to that of Example 3, compounds as set forth in Table 2 were obtained.

TABLE 2

Structure: A-CH=C(R¹)-C(=O)-N(COCH$_3$)-(CH$_2$)$_n$-[piperidine]-NCH$_2$-phenyl

| Compound No. | A | R¹ | n | m.p. (°C.) | Molecular Formula | Elemental Analysis Calcd. (Found) | | |
|---|---|---|---|---|---|---|---|---|
| | | | | | | C | H | N |
| 1 | phenyl | CH$_3$ | 2 | amorphous | C$_{26}$H$_{32}$N$_2$O$_2$·HCl | 70.81 (70.67 | 7.54 7.50 | 6.35 6.29) |

TABLE 2-continued

[Structure: CH=C(R¹)(ring A)—C(=O)—N(COCH₃)—(CH₂)ₙ—[cyclohexyl]—NCH₂—[phenyl]]

| Compound No. | A | R¹ | n | m.p. (°C.) | Molecular Formula | Elemental Analysis Calcd. (Found) | | |
|---|---|---|---|---|---|---|---|---|
| | | | | | | C | H | N |
| 2 | [phenyl] | C₆H₅ | 2 | amorphous | C₃₇H₃₄N₂O₂·HCl | 74.01 (73.94) | 7.01 (6.99) | 5.57 (5.54) |

FORMULATION EXAMPLE 1

| | |
|---|---|
| (1) (E)-3-phenyl-N-[2-(1-benzylpiperidin-4-yl)ethyl]-2-propenamide.hydrochloride | 1 g |
| (2) lactose | 197 g |
| (3) corn starch | 50 g |
| (4) magnesium stearate | 2 g |

The above ingredients (1), (2) and corn starch (20 g) were mixed. The mixture was granulated with a paste from corn starch (15 g) and water (25 ml). To the granules was added corn starch (15 g), and the mixture was compressed with a tableting machine into 2000 tablets (3 mm diameter), each containing 0.5 mg of (1).

FORMULATION EXAMPLE 2

| | |
|---|---|
| (1) (E)-3-phenyl-N-[2-(1-benzylpiperidin-4-yl)ethyl]-2-propenamide.hydrochloride | 2 g |
| (2) lactose | 196 g |
| (3) corn starch | 50 g |
| (4) magnesium stearate | 2 g |

The above ingredients (1), (2) and corn starch (20 g) were mixed. The mixture was granulated with a paste prepared from corn starch (20 g) and water (25 ml). To the granules were added corn starch (15 g) and (4), and the mixture was compressed into 2000 tablets (5 mm diameter), each containing 1 mg of (1).

EXPERIMENTAL EXAMPLE

Cholinesterase activity was measured radiometrically by the method of Johnson and Russell[1], modified by Kleinberger and Yanai[2], with a slight modification.

S₁ fraction of the cerebral cortex of male Wistar rats, the enzyme source, was preincubated in a scintillation vial with drugs for 15 min at room temperature, and then [acetyl-³H]-acetylcholine (final 200 μM) was added and incubated further for 30 min. The reaction was terminated by adding solution containing 1 M chloroacetic acid, followed by toluene-based scintillant, and the vials were capped and shaken to transfer the product, [³H]-acetic acid, to toluene phase. Then radioactivity in the toluene phase was counted by liquid scintillation spectrometry. Inhibitory activity of the test drug was expressed by 50%-inhibitory concentration (IC₅₀), which was calculated by linear regression of log-probit transformation of the inhibition curve. By the same method, cholinesterase activity of physostigmine was measured.

1) C. D. Johnson and R. L. Russell (1975) Anal. Biochem. 64, 229–238.

2) N. Kleinberger and J. Yanai (1985) Dev. Brain Res. 22, 113–123.

The results were shown.

TABLE 3

| Compound (Example No.) | Anti-acetylcholinesterase activity IC₅₀ (μM) |
|---|---|
| 1 | 9.6 |
| 2 | 18 |
| 3 | 0.64 |
| 4-1 | 8.1 |
| 4-2 | 3.5 |
| 4-3 | 2.0 |
| 4-4 | 9.9 |
| 4-5 | 13 |
| 4-6 | 2.6 |
| 4-7 | 1.2 |
| 4-8 | 2.8 |
| 4-9 | 3.3 |
| 4-10 | 1.6 |
| 4-11 | 15 |
| 4-12 | 9.2 |
| physostigmine | 0.22 |

What is claimed is:

1. A compound of the formula:

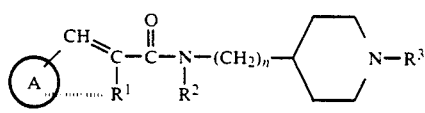

or a physiologically acceptable salt thereof,
wherein ring A is a benzene, naphthalene, anthracene, thiophene, furan, pyrazole, thiazole, isothiazole, oxazole, isoxazole, imidazole, triazole, tetrazole, pyridine, pyrimidine or pyridazine ring which is unsubstituted or substituted with 1, 2, or 3 groups of the class consisting of $C_{1-4}$ alkyl, halogen, nitro, cyano, acetylamino, $C_{1-4}$ alkoxy, $C_{1-6}$ alkylsulfonyl, methoxycarbonyl and ethoxycarbonyl, or substituted with a group Q of the class consisting of phenyl, benzyl, benzoyl, benzoylamino, benzylsulfonyl, phenylsulfonylamino, benzylsulfonylamino and phenylcarbamoyl which group Q is unsubstituted or further substituted by 1 to 3 members of the class consisting of $C_{1-4}$ alkyl, phenyl, halogen, hydroxy, benzyloxy, amino, mono- or di-$C_{1-4}$ alkylamino, nitro and $C_{1-4}$ alkoxycarbonyl;

$R^1$ is (i) hydrogen;

(ii) $C_{1-11}$ alkyl, $C_{2-4}$ alkenyl, $C_{2-4}$ alkynyl, $C_{3-7}$ monocycloalkyl, $C_{8-14}$ bicycloalkyl, adamantan-1-yl, phenyl or naphthyl, each of which is unsubstituted or substituted with 1, 2, or 3 groups of the class consisting of halogen, nitro, nitrile, hydroxy, $C_{1-4}$ alkoxy, $C_{1-4}$ alkylthio, amino, mono- or di-$C_{1-4}$ alkylsubstituted amino, $C_{1-4}$ alkoxycarbonyl, hydroxycarbonyl, $C_{1-6}$ alkylcarbonyl carbamoyl, mono- or di-$C_{1-4}$ alkyl substituted carbamoyl, adamantan-1-yl and phenyl, naphthyl, phenoxy, benzoyl, phenoxycarbonyl and phenyl $C_{1-4}$ alkylcarbamoyl each of which is unsubstituted or substituted with 1 to 4 substituents of the class consisting of $C_{1-4}$ alkyl, halogen, hydroxy, benzyloxy, amino, mono- or di-$C_{1-4}$ alkyl-substituted amino, nitro, and $C_{1-4}$ alkoxycarbonyl; or (iii) $R^1$ and the adjacent group

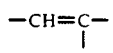

form a carbocyclic ring together with two carbon atoms constituting the ring A, as represented by the formula

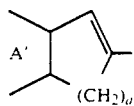

wherein a is an integer from 1 to 3 provided that A cannot be benzene when, simultaneously, a is 1; $R^2$ is hydrogen, alkyl or phenyl; and $R^3$ is phenyl or phenylalkyl;

$R^2$ is (i) hydrogen, (ii) $C_{1-11}$ alkyl, $C_{2-4}$ alkenyl, $C_{2-4}$ alkynyl, $C_{3-7}$ monocycloalkyl, $C_{8-14}$ bicycloalkyl, adamantan-1-yl, phenyl, naphthyl, $C_{1-6}$ alkylcarbonyl, $C_{3-8}$ cycloalkylcarbonyl, $C_{3-8}$ cycloalkyl-$C_{1-6}$ alkylcarbonyl, $C_{2-6}$ alkenylphenylcarbonyl, mono- or di-$C_{1-4}$ alkylcarbamoyl, mono- or di-$C_{3-6}$ alkenylcarbamoyl, mono- or di-$C_{3-6}$ alkynylcarbamoyl, phenylcarbamoyl, sulfonyl, $C_{1-6}$ alkylsulfonyl, $C_{2-6}$ alkenylsulfonyl, phenylsulfonyl, naphthylsulfonyl, $C_{1-6}$ alkyloxycarbonyl, $C_{3-8}$ cycloalkyloxycarbonyl, $C_{2-7}$ alkenyloxycarbonyl, $C_{2-7}$ alkynyloxycarbonyl, phenyloxycarbonyl, or phenyl-$C_{1-3}$ alkyloxycarbonyl, each of which is unsubstituted or substituted with 1, 2, or 3 groups of the class consisting of halogen, nitro, nitrile, hydroxy, $C_{1-4}$ alkoxy, $C_{1-4}$ alkylthio, amino, mono- or di-$C_{1-4}$ alkylsubstituted amino, $C_{1-4}$ alkoxycarbonyl, hydroxycarbonyl, $C_{1-6}$ alkylcarbonyl, carbamoyl, mono- or di-$C_{1-4}$ alkyl substituted carbamoyl, adamantan-1-yl, and phenyl, naphthyl, phenoxy, benzoyl, phenoxycarbonyl and phenyl $C_{1-4}$ alkylcarbamoyl each of which is unsubstituted or substituted with 1 to 4 substituents of the class consisting of $C_{1-4}$ alkyl, halogen, hydroxy, benzyloxy, amino, mono- or di- $C_{1-4}$ alkyl-substituted amino, nitro, and $C_{1-4}$ alkoxycarbonyl;

$R^3$ is phenyl, naphthyl, or phenyl-$C_{1-3}$ alkyl; and n is an integer from 2 to 6.

2. A compound according to claim 1 of the structural formula:

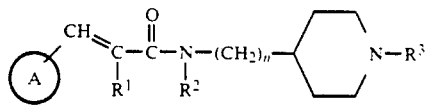

or a physiologically acceptable salt thereof, wherein ring A is a benzene, naphthalene, anthracene, thiophene, furan, pyrazole, thiazole, isothiazole, oxazole, isoxazole, imidazole, triazole, tetrazole, pyridine, pyrimidine or pyridazine ring which is unsubstituted or substituted with 1, 2, or 3 groups of the class consisting of $C_{1-4}$ alkyl, halogen, nitro, cyano, acetylamino, $C_{1-4}$ alkoxy, $C_{1-6}$ alkylsulfonyl, methoxycarbonyl and ethoxycarbonyl, or substituted with a group Q of the class consisting of phenyl, benzyl, benzoyl, benzoylamino, benzylsulfonyl, phenylsulfonylamino, benzylsulfonylamino and phenylcarbamoyl which group Q is unsubstituted or further substituted by 1 to 3 members of the class consisting of $C_{1-4}$ alkyl, phenyl, halogen, hydroxy, benzyloxy, amino, mono- or di-$C_{1-4}$ alkylamino, nitro and $C_{1-4}$ alkoxycarbonyl;

$R^1$ is hydrogen, $C_{1-11}$ alkyl, $C_{2-4}$ alkenyl, $C_{2-4}$ alkynyl, $C_{3-7}$ monocycloalkyl, $C_{8-14}$ bicycloalkyl, adamantan-1-yl, phenyl or naphthyl;

$R^2$ is hydrogen, $C_{1-11}$ alkyl, $C_{2-4}$ alkenyl, $C_{2-4}$ alkynyl, $C_{3-7}$ monocycloalkyl, $C_{8-14}$ bicycloalkyl, adamantan-1-yl, phenyl, naphthyl, $C_{1-6}$ alkylcarbonyl, $C_{3-8}$ cycloalkylcarbonyl, $C_{3-8}$ cycloalkyl-$C_{1-6}$ alkylcarbonyl, $C_{2-6}$ alkenyl-phenylcarbonyl, mono- or di-$C_{1-4}$ alkylcarbamoyl, mono- or di-$C_{3-6}$ alkenylcarbamoyl, mono- or di-$C_{3-6}$ alkynylcarbamoyl, phenylcarbamoyl, sulfonyl, $C_{1-6}$ alkylsulfonyl, $C_{2-6}$ alkenylsulfonyl, phenylsulfonyl, naphthylsulfonyl, $C_{1-6}$ alkyloxycarbonyl, $C_{3-8}$ cyclooxycarbonyl, $C_{2-7}$ alkenyloxycarbonyl, $C_{2-7}$ alkynyloxycarbonyl, phenyloxycarbonyl, phenyl-$C_{1-3}$ alkyloxycarbonyl;

$R^3$ is phenyl, naphthyl or phenyl-$C_{1-3}$ alkyl; and n is an integer from 2 to 6.

3. A compound of the structural formula

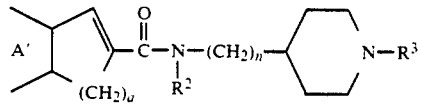

or a physiologically acceptable salt thereof, wherein ring A is a benzene, naphthalene, anthracene, thiophene, furan, pyrazole, thiazole, isothiazole, oxazole, isoxazole, imidazole, triazole, tetrazole, pyridine, pyrimidine or pyridazine ring which is unsubstituted or substituted with 1, 2, or 3 groups of the class consisting of $C_{1-4}$ alkyl, halogen, nitro, cyano, acetylamino, $C_{1-4}$ alkoxy, $C_{1-6}$ alkylsulfonyl, methoxycarbonyl and ethoxycarbonyl, or substituted with a group Q of the class consisting of phenyl, benzyl, benzoyl, benzoylamino, benzylsulfonyl, phenylsulfonylamino, benzylsulfonylamino and phenylcarbamoyl which group Q is unsubstituted or further substituted by 1 to 3 members of the class consisting of $C_{1-4}$ alkyl, phenyl, halogen, hydroxy, benzyloxy, amino, mono- or di-$C_{1-4}$ alkylamino, nitro and $C_{1-4}$ alkoxycarbonyl;

a is an integer from 1 to 3;

$R^2$ is hydrogen, $C_{1-11}$ alkyl, $C_{2-4}$ alkenyl, $C_{2-4}$ alkynyl, $C_{3-7}$ monocycloalkyl, $C_{8-14}$ bicycloalkyl, adamantan-1-yl, phenyl, naphthyl, $C_{1-6}$ alkylcarbonyl, $C_{3-8}$ cycloalkylcarbonyl, $C_{3-8}$ cycloalkyl-$C_{1-6}$ alkylcarbonyl, $C_{2-6}$ alkenyl-phenylcarbonyl, mono- or di-$C_{1-4}$ alkylcarbamoyl, mono- or di-$C_{3-6}$ alkenylcarbamoyl, mono- or di-$C_{3-6}$ alkynylcarbamoyl, phenylcarbamoyl, sulfonyl, $C_{1-6}$ alkylsulfonyl, $C_{2-6}$ alkenylsulfonyl, phenylsulfonyl, naphthylsulfonyl, $C_{1-6}$ alkyloxycarbonyl, $C_{3-8}$ cyclooxycarbonyl, $C_{2-7}$ alkenyloxycarbonyl, $C_{2-7}$ alkynyloxycarbonyl, phenyloxycarbonyl, phenyl-$C_{1-3}$ alkyloxycarbonyl;

$R^3$ is phenyl, naphthyl or phenyl-$C_{1-3}$ alkyl; and n is an integer from 2 to 6.

4. A compound according to claim 2, wherein ring A is a benzene, pyridine, furan or thiophene ring which is unsubstituted or substituted with 1 or 2 groups of the class consisting of $C_{1-4}$ alkyl, $C_{1-4}$ alkoxy, nitro, cyano, halogen and $C_{1-6}$ alkylsulfonyl; $R^1$ is hydrogen, $C_{1-6}$ alkyl or phenyl; $R^2$ is hydrogen, $C_{1-6}$ alkyl or $C_{1-6}$ alkylcarbonyl; $R^3$ is benzyl; and n is 2.

5. A compound according to claim 2, wherein ring A is a benzene, pyridine, furan or thiophene ring which is unsubstituted or substituted with $C_{1-4}$ alkoxy; $R^1$ is hydrogen, $C_{1-6}$ alkyl or phenyl; $R^2$ is hydrogen, $C_{1-6}$ alkyl or $C_{1-6}$ alkylcarbonyl; $R^3$ is benzyl, and n is 2.

6. A compound according to claim 3, wherein A is a benzene ring which is substituted with 2 groups of $C_{1-4}$ alkoxy; a is 2; $R^2$ is hydrogen; $R^3$ is benzyl; and n is 2.

7. A compound according to claim 2, wherein ring A is benzene; $R^1$ is hydrogen; $R^2$ is hydrogen, $C_{1-6}$ alkyl or $C_{1-6}$ alkylcarbonyl; $R^3$ is benzyl; and n is 2.

8. A compound according to claim 2, which is (E)-3-phenyl-N-acetyl-N-[2-(1-benzylpiperidin-4-yl)ethyl]-2propenamide.hydrochloride.

9. A compound according to claim 2, which is (E)-3-(3-pyridyl)-N-[2-(1-benzylpiperidin-4-yl) ethyl]-2-propenamide.

10. A compound according to claim 2, which is 3,4-dihydro-6,7-dimethoxy-N-[2-(1-benzylpiperidin-4-yl)ethyl]naphthalene-2-carboxamide.hydrochloride;

11. A pharmaceutical composition which contains an effective cholinesterase antagonizing amount of a compound of claim 1 and a pharmaceutically acceptable carrier or diluent therefor.

12. A compound according to claim 1 of the structural formula:

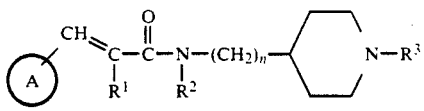

or a physiologically acceptable salt thereof. wherein ring A is a benzene, naphthalene, anthracene, thiophene, furan, pyrazole, thiazole, isothiazole, oxazole, isoxazole, imidazole, triazole, tetrazole, pyridine, pyrimidine or pyridazine ring which is unsubstituted or substituted with 1,2, or 3 groups of the class consisting of $C_{1-4}$ alkyl, halogen, nitro, cyano, acetylamino, $C_{1-4}$ alkoxy, $C_{1-6}$ alkylsulfonyl, methoxycarbonyl and ethoxycarbonyl, or substituted with a group Q of the class consisting of phenyl, benzyl, benzoyl, benzoylamino, benzylsulfonyl, phenylsulfonylamino, benzylsulfonylamino and phenylcarbamoyl which group Q is unsubstituted or further substituted by 1 to 3 members of the class consisting of $C_{1-4}$ alkyl, phenyl, halogen, hydroxy, benzyloxy, amino, nono- or di-$C_{1-4}$ alkylamino, nitro and $C_{1-4}$ alkoxycarbonyl;

$R^1$ is hydrogen, $C_{1-11}$ alkyl, $C_{2-4}$ alkenyl, $C_{2-4}$ alkynyl, $C_{3-7}$ monocycloalkyl, $C_{8-14}$ bicycloalkyl, adamantan-1-yl, phenyl or naphthyl;

$R^2$ is hydrogen, $C_{1-11}$ alkyl, $C_{2-4}$ alkenyl, $C_{2-4}$ alkynyl, $C_{3-7}$ monocycloalkyl, $C_{8-14}$ bicycloalkyl, adamantan-1-yl, phenyl, naphthyl, $C_{1-6}$ alkylcarbonyl, $C_{3-8}$ cycloalkylcarbonyl, $C_{3-8}$ cycloalkyl-$C_{1-6}$ alkylcarbonyl, $C_{2-6}$ alkenyl-phenylcarbonyl, mono- or di-$C_{1-4}$ alkylcarbamoyl, mono- or di-$C_{3-6}$ alkenylcarbamoyl, mono- or di-$C_{3-6}$ alkynylcarbamoyl, phenylcarbamoyl, sulfonyl, $C_{1-6}$ alkylsulfonyl, $C_{2-6}$ alkenylsulfonyl, phenylsulfonyl, naphthylsulfonyl, $C_{1-6}$ alkyloxycarbonyl, $C_{3-8}$ cycloalkyloxycarbonyl, $C_{2-7}$ alkenyloxycarbonyl, $C_{2-7}$ alkynyloxycarbonyl, phenyloxycarbonyl, phenyl-$C_{1-3}$ alkyloxycarbonyl, provided that if A is benzene, thiophene, furan or pyridine and $R^2$ is hydrogen, $R^1$ is not hydrogen;

$R^3$ is phenyl, naphthyl or phenyl-$C_{1-3}$ alkyl; and n is an integer from 2 to 6.

13. A compound according to claim 1, which is (E)-3-phenyl-N-[2-(1-benzylpiperidin-4-yl)ethyl]-2 -propenamide or its hydrochloride.

14. A compound according to claim 1, wherein A is 3-pyridyl, $R^1$ and $R^2$ are hydrogen; $R^3$ is benzyl and n is 2 or its hydrochloride.

15. A compound according to claim 1, wherein A is 2-furyl, $R^1$ and $R^2$ are hydrogen; $R^3$ is benzyl and n is 2 or its hydrochloride.

16. A compound according to claim 1, wherein A is thienyl, $R^1$ and $R^2$ are hydrogen; $R^3$ is benzyl and n is 2 or its hydrochloride.

17. A compound according to claim 1, wherein A is 3,4-dimethoxyphenyl, $R^1$ and $R^2$ are hydrogen; $R^3$ is benzyl and n is 2 or its hydrochloride.

18. A compound according to claim 1, wherein A is 4-nitrophenyl, $R^1$ and $R^2$ are hydrogen; $R^3$ is benzyl and n is 2 or its hydrochloride.

19. A compound according to claim 1, wherein A is 4-cyanophenyl, $R^1$ and $R^2$ are hydrogen; $R^3$ is benzyl and n is 2 or its hydrochloride.

20. A compound according to claim 1, wherein A is 4-methylsulfonylphenyl, $R^1$ and $R^2$ are hydrogen; $R^3$ is benzyl and n is 2.

21. A compound according to claim 1, wherein A is 4-tolylphenyl, $R^1$ and $R^2$ are hydrogen; $R^3$ is benzyl and n is 2.

22. A compound according to claim 1, wherein A is 4-chlorophenyl, $R^1$ and $R^2$ are hydrogen; $R^3$ is benzyl and n is 2 or its hydrochloride.

* * * * *